(12) United States Patent
Björling

(10) Patent No.: US 6,915,158 B2
(45) Date of Patent: Jul. 5, 2005

(54) CARDIAC STIMULATING DEVICE WITH MORPHOLOGY SENSITIVE DETECTION AND METHOD FOR AUTOMATICALLY CREATING A MORPHOLOGY TEMPLATE

(75) Inventor: Anders Björling, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 390 days.

(21) Appl. No.: 09/993,156

(22) Filed: Nov. 19, 2001

(65) Prior Publication Data

US 2002/0183640 A1 Dec. 5, 2002

(51) Int. Cl.$^7$ .............................................. A61B 5/0452
(52) U.S. Cl. .................................................... 600/517
(58) Field of Search .............................. 600/508–518; 607/4, 5, 9, 27, 25

(56) References Cited

U.S. PATENT DOCUMENTS

| | | | |
|---|---|---|---|
| 4,336,810 A | | 6/1982 | Anderson et al. |
| 4,905,708 A | | 3/1990 | Davies |
| 5,086,772 A | * | 2/1992 | Larnard et al. ................ 607/4 |
| 5,240,009 A | * | 8/1993 | Williams .................... 600/515 |
| 5,280,792 A | * | 1/1994 | Leong et al. ............... 600/515 |
| 5,542,430 A | * | 8/1996 | Farrugia et al. ............ 600/518 |
| 5,645,070 A | * | 7/1997 | Turcott ....................... 600/515 |
| 5,666,959 A | | 9/1997 | Deans et al. |
| 5,794,624 A | * | 8/1998 | Kwong ........................ 600/515 |
| 5,796,924 A | * | 8/1998 | Errico et al. ................... 706/25 |
| 5,797,399 A | * | 8/1998 | Morris et al. ............... 600/518 |
| 6,192,273 B1 | | 2/2001 | Igel et al. |
| 6,266,554 B1 | * | 7/2001 | Hsu et al. .................... 600/515 |
| 6,684,100 B1 | * | 1/2004 | Sweeney et al. ............ 600/517 |

FOREIGN PATENT DOCUMENTS

| | | |
|---|---|---|
| EP | 0 617 980 | 10/1994 |
| WO | WO 01/67950 | 9/2001 |

OTHER PUBLICATIONS

Pacemakerdetektor med KurvigenKänning och Förbättrad Störundertryckning J. Lingman, Master Thesis and Royal Institute of Technology, Stockholm, Sweden.

* cited by examiner

*Primary Examiner*—Jeffrey R. Jastrzab
(74) *Attorney, Agent, or Firm*—Schiff Hardin LLP

(57) ABSTRACT

In a method for automatic creation of a template for a morphology sensitive detector for an implantable cardiac stimulating device and a cardiac stimulating device operating according to the method, a predetermined length of the heart signal is recorded and filtered, all deflections exceeding a predetermined amplitude are identified and stored based on the condition that selected deflections must be separated at least by a predetermined amount of time, all selected deflections are categorized into separate classes, and the most representative class or classes for creation of the template is selected.

40 Claims, 7 Drawing Sheets

CARDIAC STIMULATING DEVICE WITH MORPHOLOGY SENSITIVE DETECTION AND METHOD FOR AUTOMATICALLY CREATING A MORPHOLOGY TEMPLATE

BACKGROUND OF THE INVENTION

1. Field of the Invention

The present invention relates to an implantable stimulating device of the type having a morphology sensitive detector for detection of electrical signals originating from the heart. The invention also relates to a method for automatic creation of a template or reference signal for a morphology sensitive detector for cardiac signals.

2. Description of the Prior Art

The use of morphology sensitive detectors that compare heart signals to a template as a tool to determine the actual heart rhythm is known.

U.S. Pat. No. 5,797,399 discloses a pattern recognition system for use in an implantable cardioverter defibrillator for differentiating between normal and abnormal heart beats. A template standard is established that defines a median or other statistical measure of "central tendency" above which or below which actual sample values would be notable.

U.S. Pat. No. 5,280,792 discloses a method for automatically classifying intracardiac electrograms and a system for performing the method. The method employs neural networks which are trained through the use of supervised training with signals representative for arrhythmia and for normal sinus rhythm.

U.S. Pat. No. 5,240,009 discloses a medical device with morphology discrimination. The intracardiac electrogram is identified by determining, with respect to a waveform peak of the intracardiac electrogram, its amplitude, width and polarity. The identification criteria are averaged and stored to provide a standard complex. Subsequent complexes are compared to the stored standard complex. Such comparison includes comparing peaks of subsequent complexes with the peaks of a stored standard complex, aligning subsequent complexes with a stored standard complex, and providing a score associated with the comparisons and alignment.

U.S. Pat. No. 5,645,070 discloses a method of discriminating among cardiac rhythms of supraventricular and ventricular origin by exploiting the differences in their underlying dynamics reflected in the morphology of the waveform. A first cardiac rhythm electrogram of known origin is sensed and a phase space representation or trajectory is generated for use as a template. The template is used for comparison with the current waveform complexes. If the difference is sufficiently different then the rhythm is deemed to be of different origin compared to the template.

U.S. Pat. No. 4,905,708 discloses an apparatus for recognizing cardiac arrhythmias that digitizes analog signals which are obtained when carrying out sensing at the heart or on the body and carries out a first differentiation of the digitalized signals. The concept is to compare the first differential of the digitized electrogram of each heartbeat with what is established to be the first differential of the digitized electrogram for normal rhythm.

In a master thesis by Joakim Lingman at the Royal Institute of Technology, Department for Signals, Sensors, & Systems, an improved heartbeat detector is disclosed. A matched filter for heart beat detection is disclosed. In order to obtain a template for the matched filter, a prerecorded digitized IEGM of a certain length is divided into three parts. Around the sample value with the highest negative derivative a window is chosen. The convolution between these three possible QRS complexes and the total signal are then calculated. The complex generating the three largest values from the convolution is chosen as the template. Convolution may be described as a multiplication of all samples in two curves and then adding the products to a convolution sum. The convolution sum reaches a maximum if the two curves are identical.

SUMMARY OF THE INVENTION

An object of the present invention is to provide an improved fully automatic method for creation of a heart signal template for use in the heart signal detector in an implantable medical device such as a pacemaker.

The above object is achieved in accordance with the principles of the present invention in a method for automatic creation of a template for a morphology-sensitive detector for an implantable cardiac stimulating device, and a cardiac stimulating device operating according to the method, a predetermined length (duration) of the heart signal is recorded and filtered, all deflections exceeding a predetermined amplitude are identified and stored based on the condition that the selected deflections must be separated at least by a predetermined amount of time, all of the selected deflections are categorized into separate classes, and the most representative class or classes for creation of the template is selected.

DESCRIPTION OF THE PREFERRED EMBODIMENTS

Figure 1:
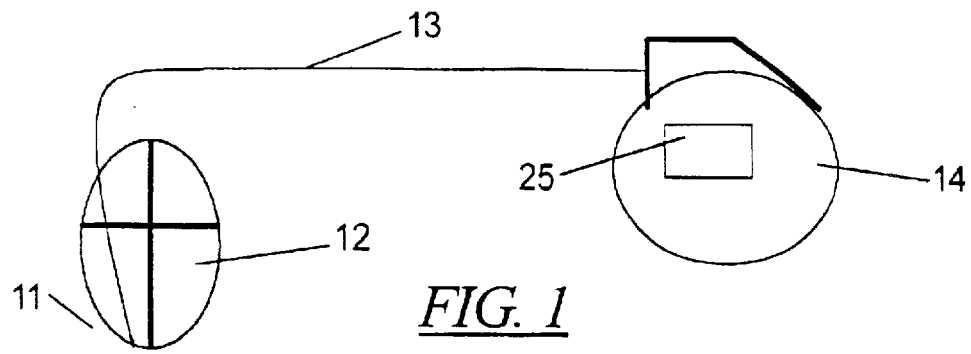
FIG. 1 shows a typical pacemaker system as implanted.

FIG. 1 shows a typical pacemaker system as implanted. The pulse generator 14 is connected to the heart via a lead body 13 and an electrode 11 connected to the distal portion of the lead body 13. Signals from a patient's heart 12 are picked up by the electrode 11 and transferred to the pulse generator 14 by the lead body 13. Stimulation pulses from the pulse generator 14 are transferred to the heart 12 via lead body 13 and electrode 11. The pacemaker also includes a heart signal detector 25. The present invention forms a part of this heart signal detector.

Figure 2:
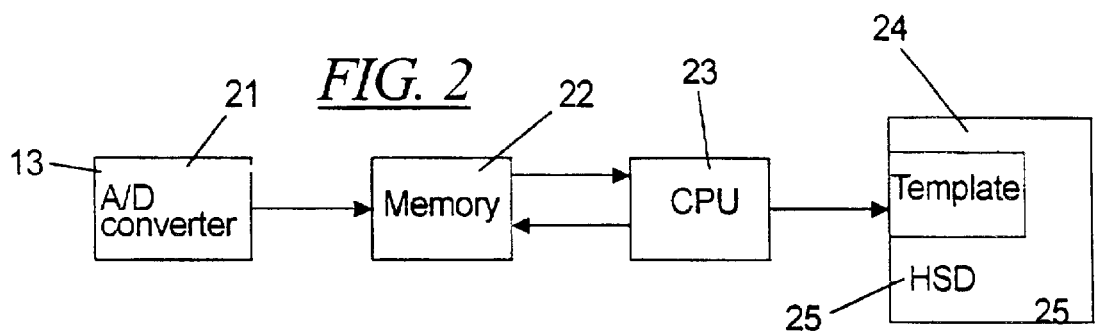
FIG. 2 shows a typical hardware implementation for the invention.

FIG. 2 shows a signal processing hardware block diagram that can be used to implement the invention, including the lead body 13, an A/D-converter 21, a memory 22, a CPU 23 and a template storage 24 that is a part of the heart signal detector 25. Basically the processing involves two steps. The first step is when the heart signal obtained from the lead body 13 is continuously A/D converted in the A/D converter 21 and stored in a memory 22. This step corresponds to an operation that can be described as recording of an IEGM segment. In the second step different algorithms implemented as software in the CPU are applied on the signal stored in the memory 22 to create the signal template stored in the signal template storage 24 to be used by the heart signal detector 25.

Figure 3:
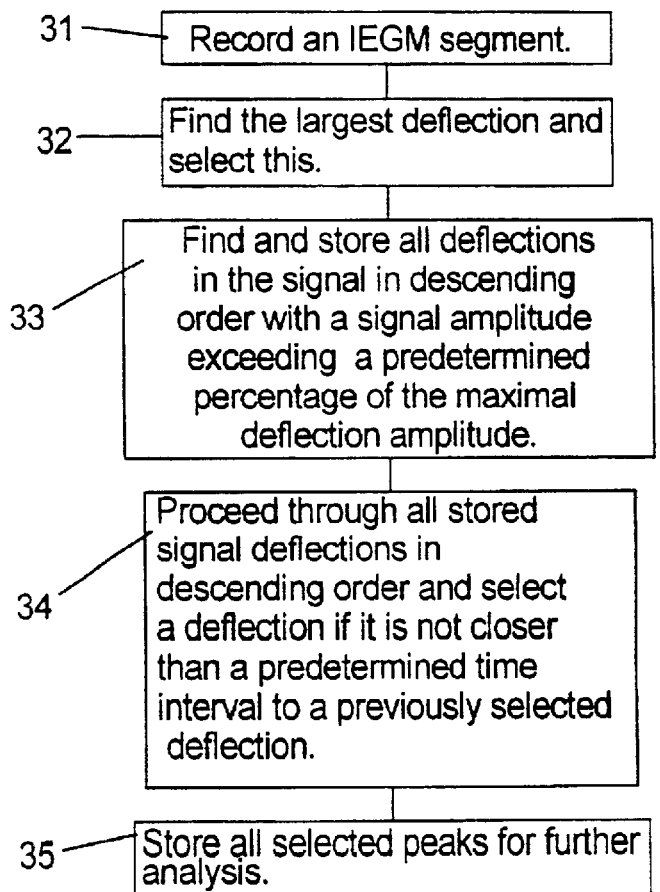
FIG. 3 shows a schematic flowchart of the most basic algorithm of the invention.

FIG. 3 shows a schematic flowchart of the first part of the algorithm to determine a template for a filter matched to a certain morphology. A matched filter is a filter that has its maximum gain for a signal identical to the template. The purpose of this diagram is to define a method to select deflections that may be QRS-complexes in an amplitude descending order. In block 31 a segment of an IEGM signal is recorded, the length of which may be in the range from a few seconds up to several minutes. Following the recording the recorded signal may be filtered in a filter suitable for intracardiac signals in order to remove noise and to enhance portions of the signal. The filtering can be made by digital filtering by the CPU 23 (FIG. 2) on the recorded signal in the memory 22 (FIG. 2) for flexibility reasons since that allows the filter parameters to be modified after recording but it would also be feasible to make the filtering through hardware filters simultaneously with the recording. In block 32 the largest deflection is identified and selected. In block 33 all deflections in the signal with an amplitude exceeding a predetermined percentage in the range of 40–75% of the maximum amplitude in the recorded signal are to be found and stored for subsequent analysis. When performing this step the maximum amplitude must be checked to be within reasonable limits. In block 34 deflections are selected in descending order. In order to reject signals which are not of physiologic origin, deflections which are closer than a predetermined time interval, e.g. approximately 350 ms to a previously selected deflection, are excluded from selection. The time interval may be in the range 200–500 ms. The selection process ends either when no more deflections will be taken into account since they fall within the time interval mentioned above, or when the amplitude of the remaining deflections are less than a predetermined percentage of the maximum signal amplitude recorded. In block 35 all selected deflections are stored for further analysis.

The final result from the process outlined in FIG. 3 is a number of possible heart signal deflections that may be used for template generation.

Figure 4:
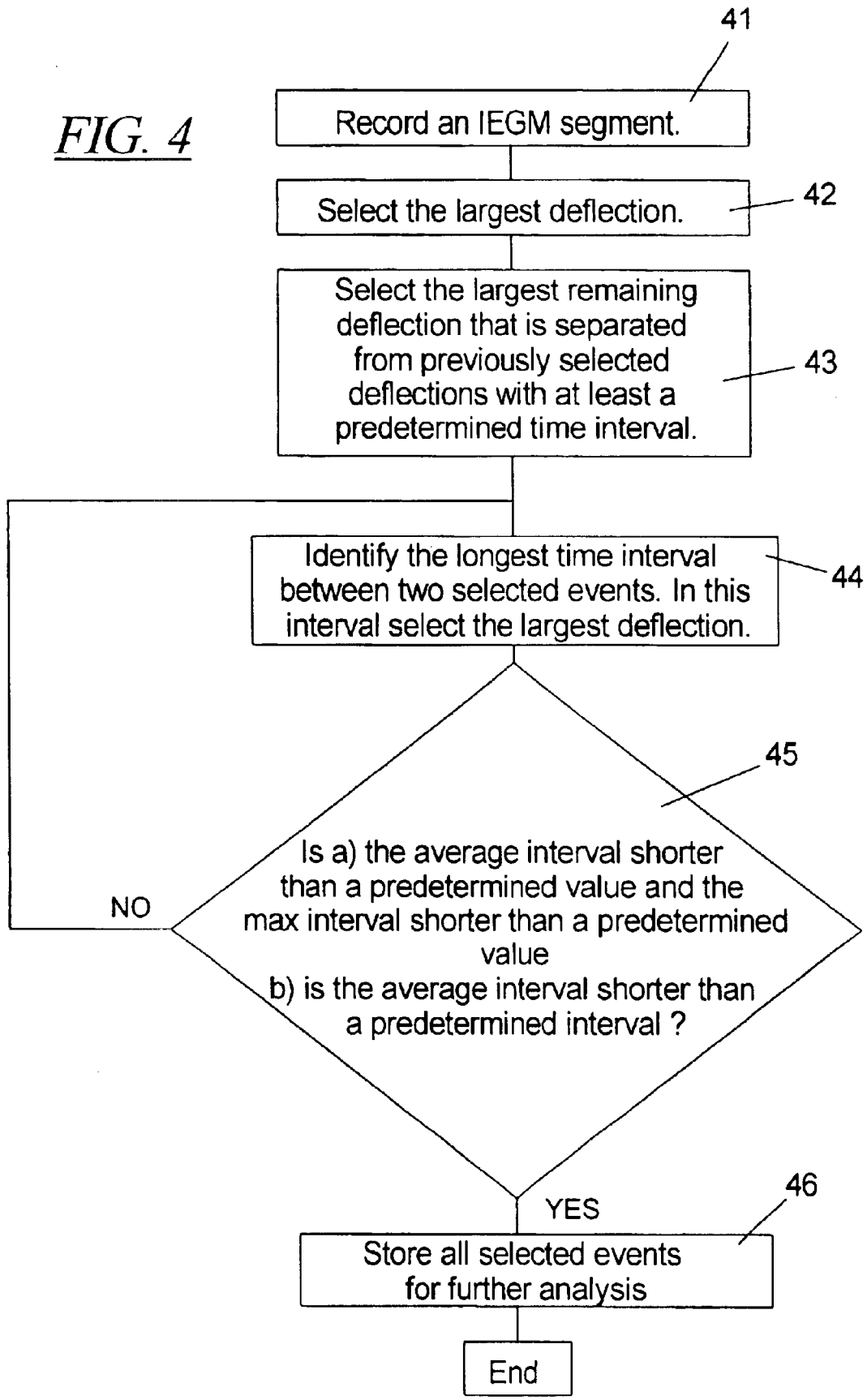
FIG. 4 shows a schematic flowchart of an implementation specifically designed to adapt to signals with a high baseline drift.

FIG. 4 is an enhanced schematic flowchart that would improve the functionality in the presence of large amplitude variations in the IEGM-signal recorded from the electrode. This is achieved by always searching for the highest deflection in the longest interval found between two previous selections.

In block 41 an IEGM segment is recorded. This is accomplished through continuous AD-conversion of the incoming signal. The AD-converted signal values are written into the memory 22 (FIG. 2). The second optional step may be to filter the recorded signal in a filter suitable for signals of cardiac origin. The filtering is typically digital filtering performed on collected data. Digital filtering means that the CPU 23 performs mathematical operations that are equivalent to filtering on the stored IEGM segment. In block 42 the largest signal deflection is selected. In block 43 the longest interval between two selected deflections or between an endpoint in the recording and a selected deflection is identified. In this interval the largest deflection is selected that is not closer to a previously selected deflection than a predetermined interval in the range of 200–500 ms.

In block 44 and in block 45 the process to identify the longest interval and to select the largest deflection in the longest interval continues until one of the two following conditions is fulfilled: a) the average interval between selected deflections is shorter than a predetermined value in the range of 1000–2000 ms and the maximum interval is shorter than a predetermined value in the range of 1500–3000 ms or b) if the average interval is shorter than an interval in the range 400–800 ms. In block 46 all selected events are stored for further analysis. The final result from the process outlined in FIG. 4 is a number of possible heart signal deflections that may be used for template generation.

Figure 5:
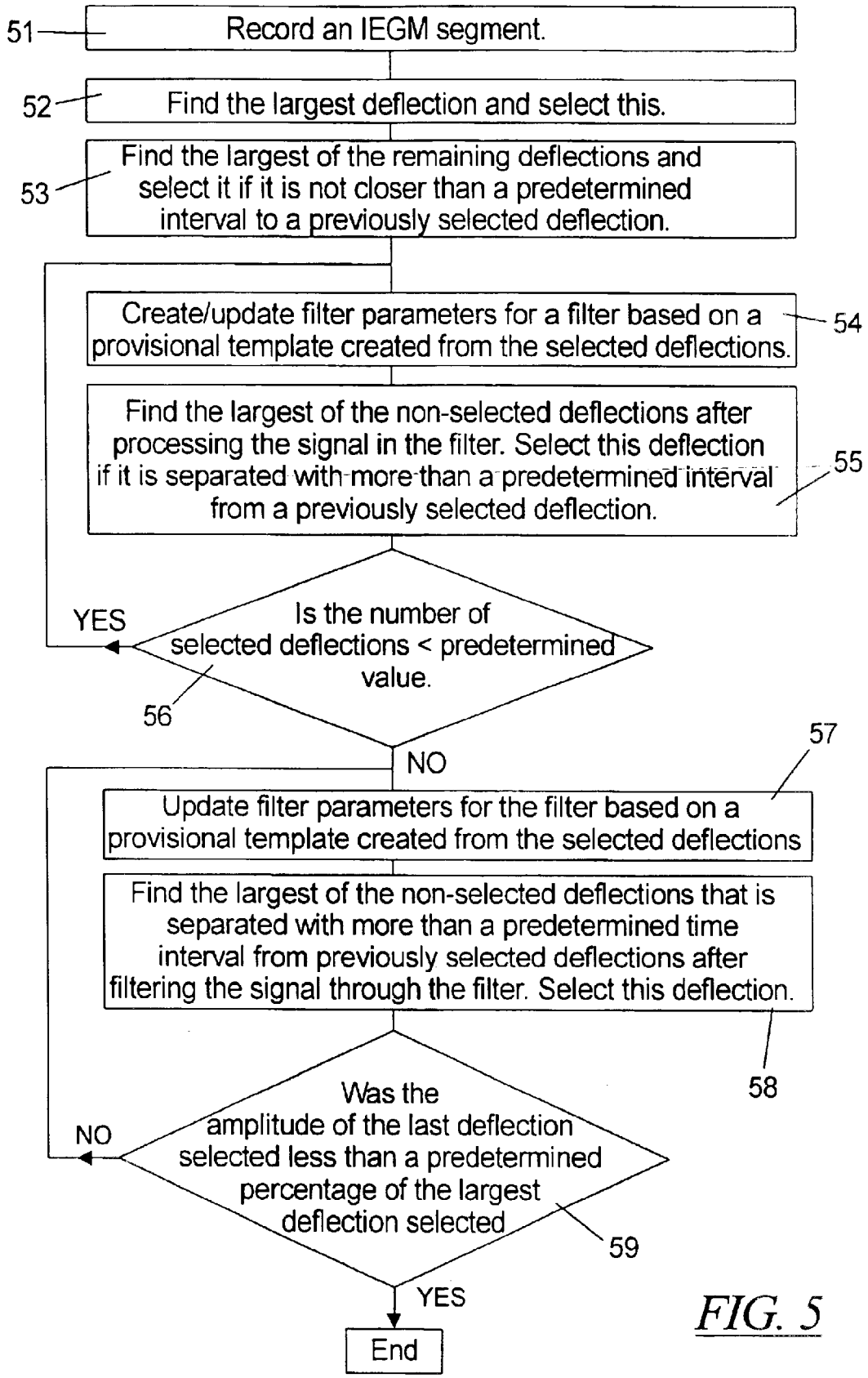
FIG. 5 shows a schematic flowchart of an implementation similar to the implementation outlined in FIG. 3 but with a filter added to improve noise rejection.

FIG. 5 represents an enhancement of the algorithm described in FIG. 2. Basically the enhancement is that a filter is introduced in the deflection selection process. In block 51 an IEGM segment is recorded that may have a duration between a few seconds up to several minutes. In block 52 the largest deflection is selected. In block 53 the largest of the remaining deflections is identified. This deflection is selected if it is not closer than a predetermined time interval in the range of 200 ms to 500 ms to the previously selected deflection. In block 54 filter parameters based on a provisional template for a filter is created based on the selected deflections. In block 55 the largest of the non-selected deflections after processing the signal in the filter is identified. This deflection is selected if it is separated more than a predetermined value in the range of 200–500 ms from a previously selected deflection. Block 56 controls that the process of updating the provisional template for the filter and selection of the largest of the not selected deflections is repeated until the number of selected deflections has reached a predetermined value in the range of 4–15. Block 57 is reached when the number of selected deflections has reached the predetermined value in the range of 4–15. In block 57 the filter parameters are updated based on a provisional template created from the selected deflections. In block 58 the largest of the not selected deflections that is separated with more than a predetermined time interval in the range of 200 ms–500 ms from previously selected deflections after filtering the signal through the filter is selected. Block 59 controls the process of updating the provisional template for creation of the filter parameters, identifying the largest of the not selected deflections after filtering that is separated with more than a predetermined time interval from previously selected deflections until the amplitude of the last deflection selected has reached a predetermined percentage in the range of 40–75% of the largest deflection selected. The final result from the process outlined in FIG. 5 is a number of possible heart signal deflections that may be used for template generation.

Figure 6:
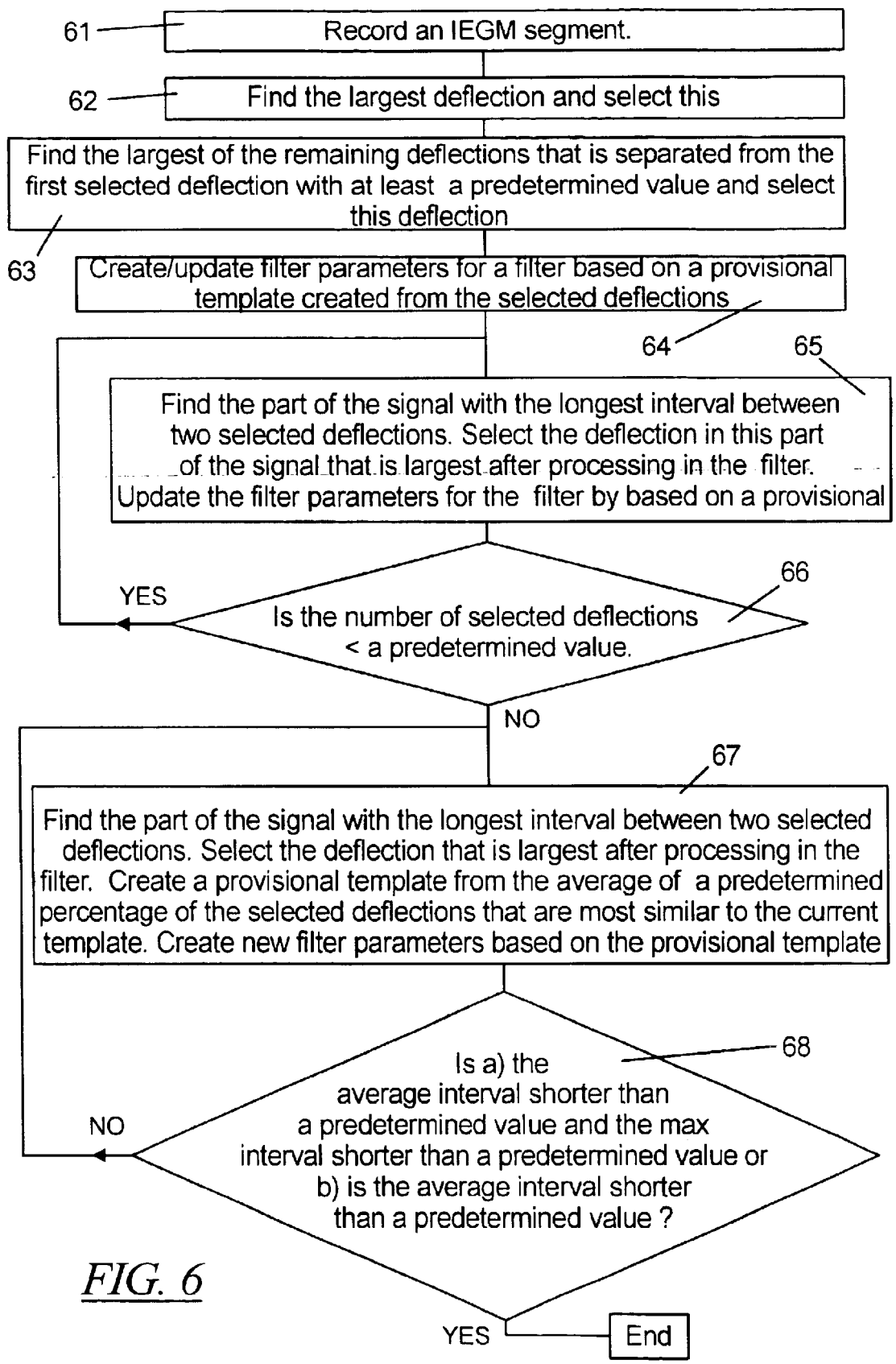
FIG. 6 shows a schematic flowchart of an implementation as outlined in FIG. 4 but with a filter added to improve noise rejection.

FIG. 6 represents an enhancement of the algorithm described in FIG. 4. Basically the enhancement is that a filter is introduced in the deflection search. In block 61 an IEGM segment is recorded that may have a duration between a few seconds up to several minutes. In block 62 the largest deflection is identified and selected. In block 63 the largest of the remaining deflections that is separated from the first selected deflection with at least a predetermined value in the range of 200–500 ms is identified and selected. In block 64 a provisional template for creation of filter parameters is created based on selected deflections through averaging. In block 65 the longest interval between two selected deflections is identified. Further in block 65 the largest deflection after processing the signal in the filter is selected. Finally the provisional template is updated based on selected deflections in block 65. In block 66 a test is performed to determine if the number of selected deflections is less than a predetermined value in the range of 4–15. Block 65 is repeated as long as the number of selected deflections is less than the predetermined number in the range of 4–15. After having reached a predetermined number in the range of 4–15 selected deflections the algorithm continues in block 67 as described above with the modification that a predetermined percentage in the range of 60–80% of the deflections selected that deviates least from the average of all selected deflections are used when the provisional template used for determination of the filter parameters is created. In block 68 the following test is performed: the process to identify the longest interval and to select the largest deflection in the longest interval continues until a) the average interval between selected deflections is shorter than a predetermined value in the range of 1000–2000 ms and the max interval is shorter than a predetermined value in the range of 1500–3000 ms or b) if the average interval is shorter than an interval in the range 400–800 ms. The final result from the process outlined in FIG. 6 is a number of possible heart signal deflections that may be used for template generation.

Figure 7:
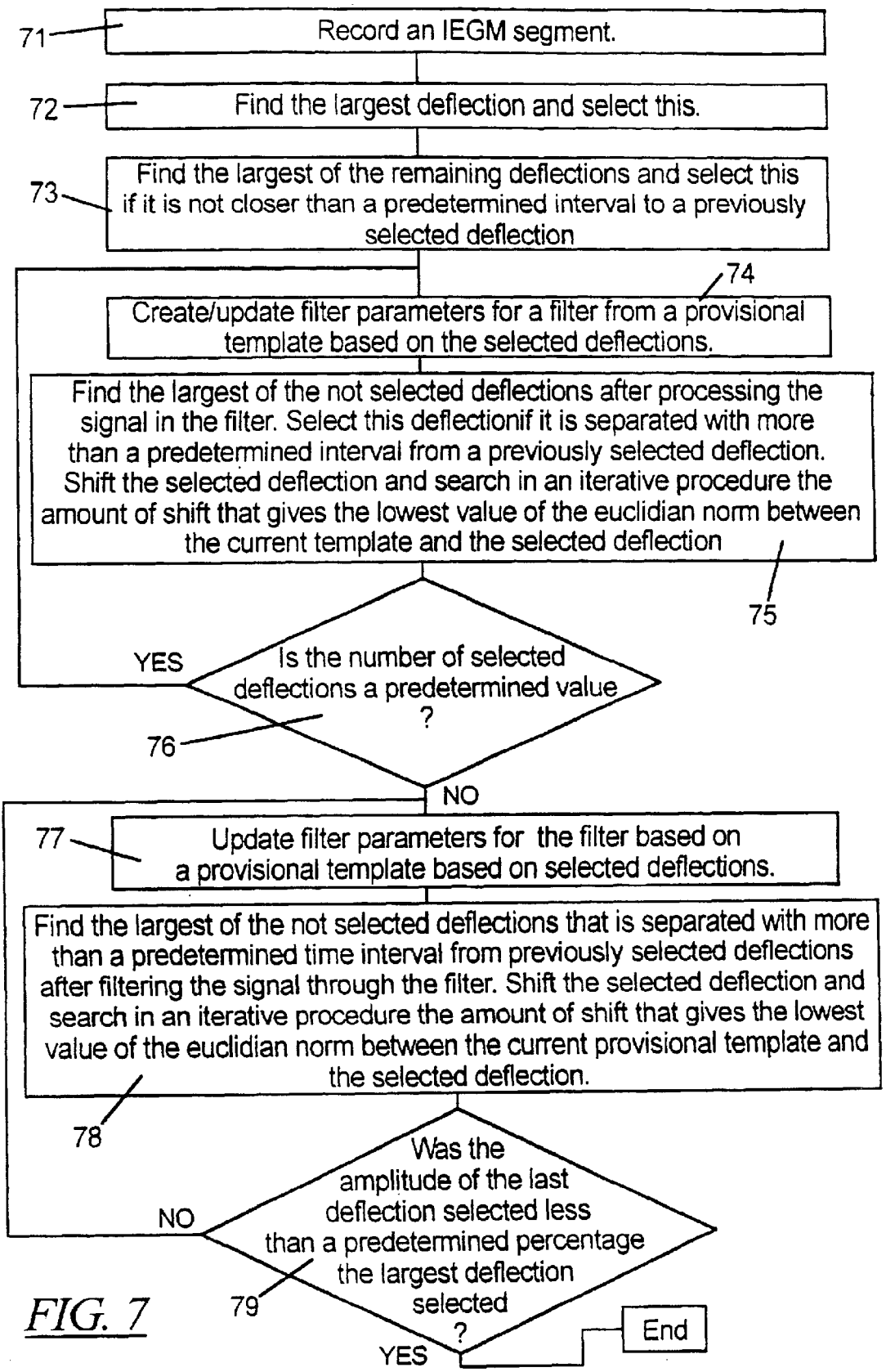
FIG. 7 shows a schematic flowchart of how the algorithm described in FIG. 5 can be improved by adding a step of shifting selected deflections for optimum alignment with the current template used by the filter before updating the template with the selected deflection.

FIG. 7 illustrates a technique to further enhance the performance of the algorithm described in FIG. 4 particularly under noisy conditions. If noise is present the peak amplitude may occur at a different point in time compared to when no noise is present. As a result the resulting template will become distorted. One possibility to minimize the effect of superimposed noise would be to shift a selected complex to the left or right and after each shift operation calculate the Euclidean norm between the selected complex and the current provisional template and select the shifted complex that gave the minimum Euclidean norm. The amount of shifting expressed in time should be limited to a predetermined interval in the range of 0–15 ms. When the provisional template is updated by adding the selected complex this will be optimally aligned to the current provisional template which will improve the quality of the updated template. Thus as soon as a deflection is selected it will be shifted for optimum alignment with the current provisional template before the selected deflection is used for provisional template updating. In block 71 an IEGM segment is recorded and stored in the memory. In block 72 the largest deflection is identified and selected. In block 73 the largest of the remaining deflections is identified and this deflection is selected if it is not closer than a predetermined interval in the range of 200–500 ms to a previously selected deflection. In block 74 a provisional template for the filter is created based on the selected deflections. In block 75 the largest of the not selected deflections after processing the signal in the matched filter is identified. This deflection is selected if it is separated with more than a predetermined time interval from previously selected deflections. Further in block 75 the Euclidean distance is calculated between the current provisional template and the selected deflection. The selected deflection is shifted back and forth in an iterative procedure until the lowest value of the Euclidean distance is found. In block 76 a test is performed to determine if the next block to be processed shall be block 74 or if the next block to be processed shall be block 77, if the number of selected deflections exceed a predetermined number in the range of 4–15 the next block to be processed shall be block 77 otherwise the next block to be processed shall be 74. In block 77 the provisional template for the creation of filter parameters for the filter is updated based on all selected deflections. In block 78 the largest of the not selected deflections, after filtering the deflections in the filter, that is separated with a predetermined time interval in the range of 200–500 ms from previously selected deflections is selected. This selected deflection is shifted back and forth in an iterative procedure to find the amount of shift that gives the lowest Euclidean norm between the current provisional template and the selected deflection. In block 79 a test is performed in order to determine when the search for deflections to be selected shall be terminated. When the last selected deflection has an amplitude in a predetermined range of 40–70% of the largest selected deflection no more deflections shall be selected. The final result from the process outlined in FIG. 7 is a number of possible heart signal deflections that may be used for template generation.

Figure 8:
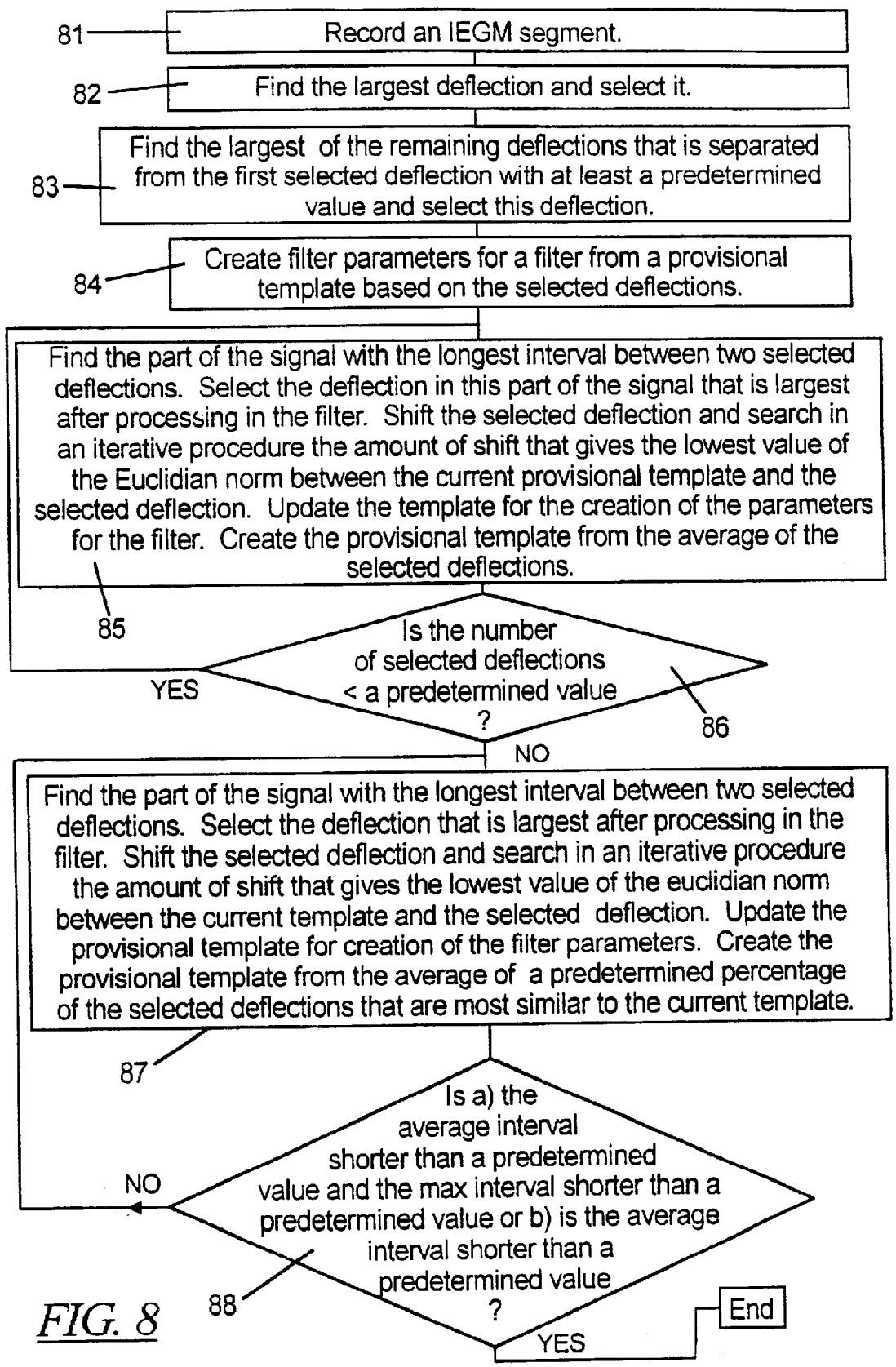
FIG. 8 shows a schematic flowchart of how the algorithm described in FIG. 6 can be improved by adding a step of shifting selected deflections for optimum alignment with the current template used by the filter before updating the template with the selected deflection.

FIG. 8 illustrates a further improvement of the algorithm in FIG. 6 in order to improve performance in the presence of noise. In block 81 an IEGM segment is recorded and stored in the memory. In block 82 the largest deflection is identified and selected. In block 83 the largest of the remaining deflections is identified and this deflection is selected if it is not closer than a predetermined interval in the range of 200–500 ms to a previously selected deflection. In block 84 a provisional template for determination of filter parameters is created based on the selected deflections. In block 85 the longest interval between two selected deflections is identified. The largest deflection after processing the signal in the filter is selected if it is separated from a previously selected deflection with at least a predetermined value in the range of 200–500 ms. Further in block 85 the Euclidean distance is calculated between the current template and the selected deflection. The selected deflection is shifted back and forth in an iterative procedure until the lowest value of the Euclidean distance is found. The final activity in block 85 is to update the provisional template as an average of all selected deflections for determination of filter parameters. In block 86 a test is performed to determine if the next block to be processed shall be block 85 repeated or if the next block to be processed shall be block 87, if the number of selected deflections is less than a predetermined number in the range of 4–15 the next block to be processed shall be block 85 otherwise the next block to be processed shall be 87. In block 87 the part of the stored signal with the longest interval between two selected deflections is identified. The largest deflection after processing the signal in the matched filter is selected if it is separated from a previously selected deflection with at least a predetermined value in the range of 200–500 ms. Further in block 87 the Euclidean distance is calculated between the current provisional template and the selected deflection. The selected deflection is shifted back and forth in an iterative procedure until the lowest value of the Euclidean distance is found. Next activity in block 87 is to update the provisional template for determination of the filter parameters. The template is created from the average of a predetermined percentage in the range of 60–80% of the selected deflections that are most similar to the current template. In block 88 the following test is performed: the process to identify the longest interval and to select the largest deflection in the longest interval continues until a) the average interval between selected deflections is shorter than a predetermined value in the range of 1000–2000 ms and the max interval is shorter than a predetermined value in the range of 1500–3000 ms or b) if the average interval is shorter than an interval in the range 400–800 ms. When the criteria in the test are fulfilled the process to find deflections is finalized. The final result from the process outlined in FIG. 8 is a number of possible heart signal deflections that may be used for template generation.

Figure 9:
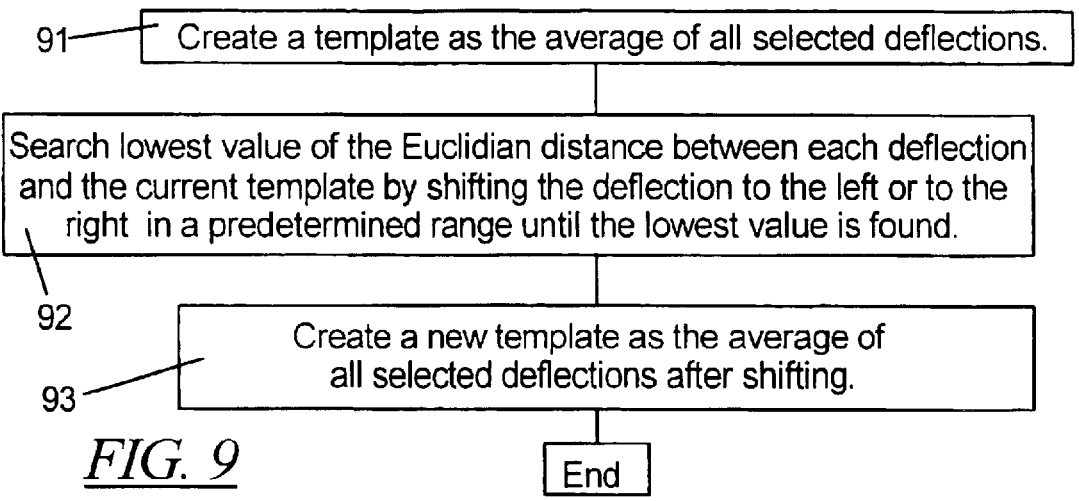
FIG. 9 shows a schematic flowchart of a shifting algorithm used to optimize the alignment between signal and template. This will potentially improve the quality of the resulting template.

FIG. 9 illustrates another way to improve the quality of the template. In block 91 a template created as an average of all selected deflections. In block 92 each deflection is shifted to find the minimum of the Euclidean norm between the selected deflection and the current template. The amount of shift allowed in block 92 is limited to ±15 ms. In block 93 a new template is created as the average of all selected deflections after shifting. The procedure in block 92 and 93 may be repeated to further improve the quality of the template. This method is applicable to improve the quality of the template regardless of how the deflections has been selected.

Figure 10:
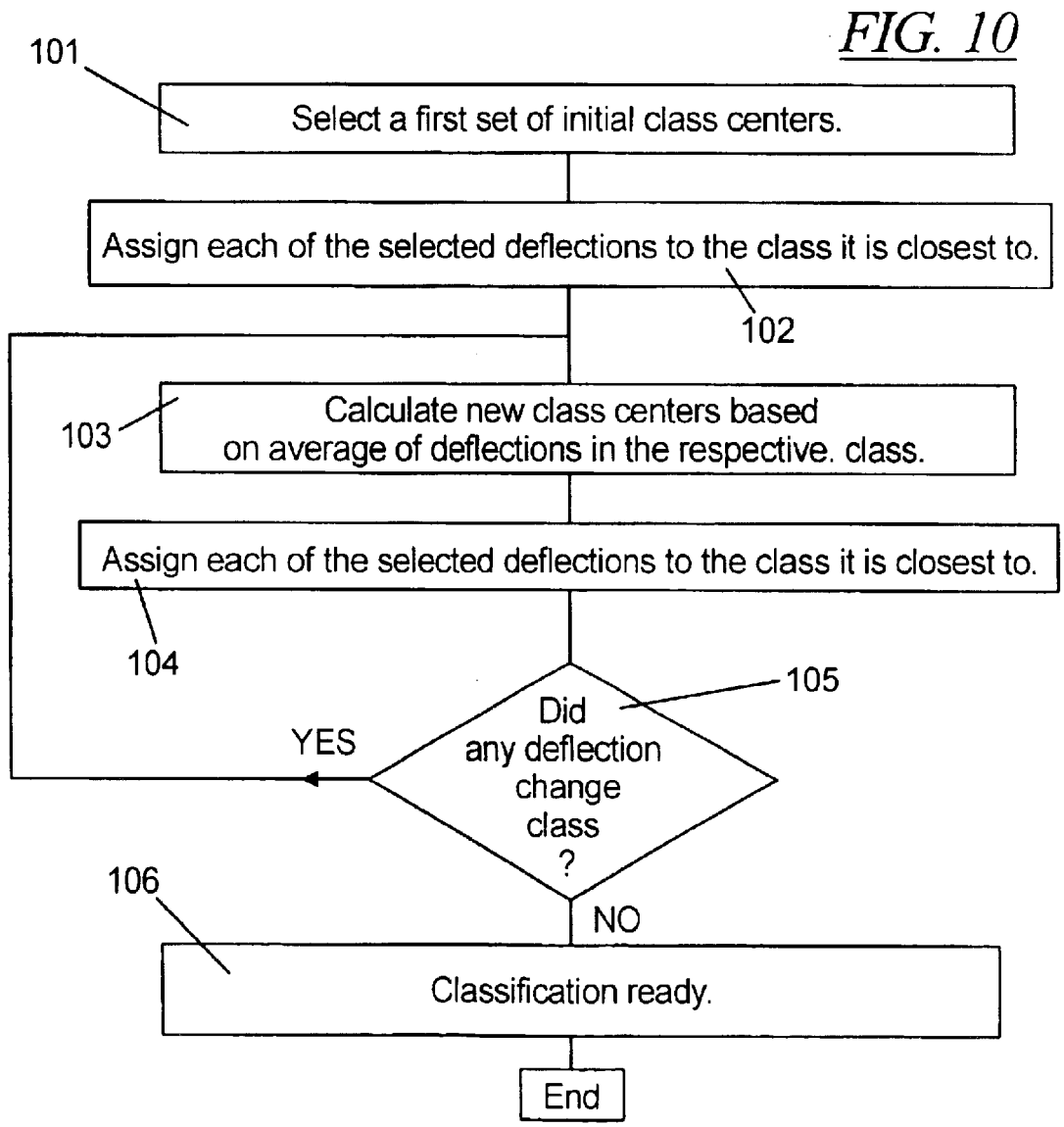
FIG. 10 shows a schematic flowchart of how selected deflections may be divided into different classes, using the generalized Lloyd algorithm, for a later determination of which class or classes that is most representative for physiologic heart signals.

In FIG. 10 a technique is provided to divide all selected deflections into classes. The idea is then to select the most QRS-like class as basis for the template. After identification and storing of deflections that may originate from these potential QRS are divided into a predetermined number of classes. The number of classes should be selected in range 1–10 and may depend on the current noise situation. In a preferred embodiment the Generalized Lloyd Algorithm (GLA) has been used for classification of the signals. FIG. 10 illustrates the application of the GLA algorithm to divide selected deflections into classes. In block 101 an initial set of class centers is selected e.g. at random. In block 102 all selected deflections are assigned to the class they are closest to. In block 103 new class centers are calculated based on the average of the deflections in respective class. In block 104 each of the selected deflections is assigned to the class it is closest to. In block 105 a test is performed to determine if the process of assigning the selected deflections to different classes can be finalized. If no deflections changed classes in the last processing of block 104 the procedure of dividing the selected deflections into classes shall be terminated otherwise the procedure of dividing the selected deflections into classes will continue with block 103.

Following the classification of the deflections the most representative class for the QRS shall be selected. Several different criteria for selection of the most representative class may be defined. High amplitude and morphological similarity has shown to be useful criteria for selection of the most representative class. In one preferred embodiment the class for which the mean amplitude divided by the normalized dissimilarity resulted in the largest number was selected as the most representative class for the creation of the template for the morphology sensitive detector. The normalized dissimilarity in a class is defined as the mean of the squared distance between the average and the individual deflections in the class. Normalization means dividing the individual deflections by the square root of the sum of the squares of the deflections in question. Other possible criteria would be to study the repetition rate for the deflections belonging to a particular class in which case deflections with a repetition rate reasonable for a beating heart would be an indicator that the class might be representative. Studying the mean maximum derivative in the class for each deflection could also be possible, a higher mean maximum derivative indicating a higher probability that the complex is a true QRS.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for automatically creating a template for a morphology-sensitive cardiac signal detector, comprising the steps of:

recording an IEGM signal from a patient for a predetermined duration, and filtering said IEGM signal in a filter, thereby obtaining a filtered IEGM signal;

storing said filtered IEGM signal, thereby obtaining a stored IEGM signal;

analyzing said stored IEGM signal to identify all signal deflections in said IEGM signal which exceed a predetermined level, to obtain preliminarily identified signal deflections;

analyzing respective time intervals between said preliminarily identified deflections and selecting deflections, as selected deflections, from among said preliminarily identified deflections dependent on said time interval;

categorizing said selected deflections into a predetermined number of classes;

determining at least one of said classes as most representative for a QRS complex;

creating a QRS template from the selected deflections in said at least one of said classes; and initializing said filter with said template for filtering subsequent IEGM signals using said template.

2. A method as claimed in claim 1 wherein said preliminarily identified deflections include a deflection having a maximum deflection amplitude, and wherein the step of analyzing the respective time intervals comprises:

selecting preliminarily identified deflections in amplitude-descending order, starting with said deflection having said maximum deflection amplitude and ending with a preliminarily identified deflection having a lowest amplitude in a predetermined percentage range of said maximum deflection amplitude and, as said preliminarily identified deflections are selected in said amplitude-descending order, excluding selection of preliminarily identified deflections in a window surrounding a previously selected preliminarily identified deflection.

3. A method as claimed in claim 2 wherein said predetermined percentage range is 40%–75% of said maximum deflection amplitude.

4. A method as claimed in claim 2 wherein said window is in a range from 200–500 ms before a previously selected preliminarily identified deflection until 200–500 ms after that previously selected preliminarily identified deflection.

5. A method as claimed in claim 1 wherein the step of creating said template comprises, from said preliminarily identified deflections, selecting a predetermined number of deflections having largest amplitudes and separated from each other by a predetermined interval, averaging said predetermined number of deflections to obtain a first preliminary template selecting a percentage of said predetermined number of deflections most similar to said preliminary template and creating an updated template from said predetermined percentage of deflections, and continually updating said template using said predetermined number of deflections most similar to the current template.

6. A method as claimed in claim 5 wherein said predetermined number is in a range between 4 and 15, wherein said predetermined interval is in a range between 200 and 500 ms, and wherein said predetermined percentage is in a range between 60% and 80%.

7. A method as claimed in claim 1 wherein the step of analyzing said preliminarily identified deflections includes gradually decreasing a sensing threshold until at least two of said preliminarily identified deflections are detected which are separated at least first by a predetermined interval, selecting said at least two preliminarily identified deflections as selected deflections, and thereby leaving a remainder of said preliminarily identified deflections, repeatedly finding a longest interval between two further preliminarily identified signal deflections in said remainder and selecting a preliminarily identified deflection in said longest interval which is separated from a previously selected preliminarily identified deflection by said first predetermined interval until one of (a) an average between selected deflections is less than a second predetermined interval and a maximum interval is less than a predetermined interval, and (b) said average interval is less than a minimum interval in a third predetermined range.

8. A method as claimed in claim 7 wherein said first predetermined interval is a range between 200–500 ms, said second predetermined interval is in a range between 1000–2000 ms, said third predetermined interval is in a range between 1500–3000 ms, and wherein said minimum interval is in a range between 400–800 ms.

9. A method as claimed in claim 1 wherein the step of filtering said IEGM signal comprises filtering said IEGM signal with a matched filter having said template, and wherein the step of creating said template comprises selecting from said preliminarily identified deflections, a predetermined number of deflections having largest amplitudes and separated from each other by a predetermined interval, averaging said predetermined number of deflections to obtain a first preliminary template selecting a percentage of said predetermined number of deflections most similar to said preliminary template and creating an updated template from said predetermined percentage of deflections, and continually updating said template using said predetermined number of deflections most similar to the current template.

10. A method as claimed in claim 9 wherein said predetermined number is in a range between 4 and 15, wherein said predetermined interval is in a range between 200 and 500 ms, and wherein said predetermined percentage is in a range between 60% and 80%.

11. A method as claimed in claim 1 comprising shifting said preliminarily identified deflections by predetermined time intervals in steps in opposite directions, and for each step identifying a Euclidean distance to a current template, and employing a shifted deflection having a smallest Euclidean distance to the current template for use in updating said current template.

12. A method as claimed in claim 11 wherein said time interval is in a range between 0 and 15 ms, and wherein said step is in a range between one and two ms.

13. A method as claimed in claim 1 comprising employing a Generalized Lloyd Algorithm to determine respective centers of said classes, for determining said at least one class most representative of a QRS complex.

14. A method as claimed in claim 1 comprising identifying said at least one class that is most representative of a QRS complex as the class having a highest morphology similarity to an actual QRS complex.

15. A method as claimed in claim 1 comprising selecting said at least one class as most representative of a QRS complex having a minimum measure of dissimilarity calculated using the Euclidean distance between class constituents.

16. A method as claimed in claim 1 comprising selecting said at least one class as most representative of a QRS complex having a largest negative magnitude.

17. A method as claimed in claim 1 comprising selecting said at least one class as most representative of a QRS complex having a largest positive magnitude.

18. A method as claimed in claim 1 comprising selecting said at least one class as most representative of a QRS complex as having a repetition rate within a normal physiological range for cardiac activity.

19. A method as claimed in claim 1 wherein the step of recording and filtering said IEGM signal comprises filtering said IEGM signal during recording thereof.

20. A method as claimed in claim 1 wherein the step of recording and filtering said IEG signal comprises filtering said IEG signal after recording thereof.

21. A cardiac stimulating device having a template for a morphology-sensitive cardiac signal detector, comprising:

circuitry for recording an IEGM signal from a patient for a predetermined duration;

a filter which filters said IEGM signal, thereby obtaining a filtered IEGM signal;

a memory for storing said filtered IEGM signal, as a stored signal;

a processor for analyzing said stored IEGM signal to identify all signal deflections in said IEGM signal which exceed a predetermined level, to obtain preliminarily identified signal deflections;

said processor being programmed to analyze respective time intervals between said preliminarily identified deflections and selecting deflections, as selected deflections from among said preliminarily identified deflections dependent on said time interval, categorize said selected deflections into a predetermined number of classes, determine at least one of said classes as most representative for a QRS complex, and create a QRS template from the selected deflections in said at least one of said classes; and said filter being initialized with said template for filtering subsequent IEGM signals using said template.

22. A cardiac stimulating device as claimed in claim 21 wherein said preliminarily identified deflections include a deflection having a maximum deflection amplitude, and wherein said processor is programmed to analyze the respective time intervals by selecting preliminarily identified deflections in amplitude-descending order, starting with said deflection having said maximum deflection amplitude and ending with a preliminarily identified deflection having a lowest amplitude in a predetermined percentage range of said maximum deflection amplitude and, as said preliminarily identified deflections are selected in said amplitude-descending order, excluding selection of preliminarily identified deflections in a window surrounding a previously selected preliminarily identified deflection.

23. A cardiac stimulating device as claimed in claim 22 wherein said predetermined percentage range is 40%–75% of said maximum deflection amplitude.

24. A cardiac stimulating device as claimed in claim 22 herein said window is in a range from 200–500 ms before a previously selected preliminarily identified deflection until 200–500 ms after that previously selected preliminarily identified deflection.

25. A cardiac stimulating device as claimed in claim 21 wherein said processor is programmed to create said template by selecting, from said preliminarily identified deflections, a predetermined number of deflections having largest amplitudes and separated from each other by a predetermined interval, averaging said predetermined number of deflections to obtain a first preliminary template selecting a percentage of said predetermined number of deflections most similar to said preliminary template and creating an updated template from said predetermined percentage of deflections, and continually updating said template using said predetermined number of deflections most similar to the current template.

26. A cardiac stimulating device as claimed in claim 25 wherein said predetermined number is in a range between 4 and 15, wherein said predetermined interval is in a range between 200 and 500 ms, and wherein said predetermined percentage is in a range between 60% and 80%.

27. A cardiac stimulating device as claimed in claim 21 wherein said processor analyzes said preliminarily identified deflections includes by gradually decreasing a sensing threshold until at least two of said preliminarily identified deflections are detected which are separated at least by a first predetermined interval, selecting said at least two preliminarily identified deflections as selected deflections, and thereby leaving a remainder of said preliminarily identified deflections, repeatedly finding a longest interval between two further preliminarily identified signal deflections in said remainder and selecting a preliminarily identified deflection in said longest interval which is separated from a previously selected preliminarily identified deflection by said first predetermined interval until one of (a) an average between selected deflections is less than a second predetermined interval and a maximum interval is less than a third predetermined interval, and (b) said average interval is less than a minimum interval in a predetermined range.

28. A cardiac stimulating device as claimed in claim 27 wherein said first predetermined interval is a range between 200–500 ms, said second predetermined interval is in a range between 1000–2000 ms, said third predetermined interval is in a range between 1500–3000 ms, and wherein said minimum interval is in a range between 400–800 ms.

29. A cardiac stimulating device as claimed in claim 21 wherein said filter is a matched filter having said template, and wherein said processor is programmed to create said template from said preliminarily identified deflections, by selecting a predetermined number of deflections having largest amplitudes and separated from each other by a predetermined interval, averaging said predetermined number of deflections to obtain a first preliminary template selecting a percentage of said predetermined number of deflections most similar to said preliminary template and creating an updated template from said predetermined percentage of deflections, and continually updating said template using said predetermined number of deflections most similar to the current template.

30. A cardiac stimulating device as claimed in claim 29 wherein said predetermined number is in a range between 4 and 15, wherein said predetermined interval is in a range between 200 and 500 ms, and wherein said predetermined percentage is in a range between 60% and 80%.

31. A cardiac stimulating device as claimed in claim 21 wherein said processor is programmed to shift said preliminarily identified deflections by predetermined time intervals in steps in opposite directions, and for each step to identify a Euclidean distance to a current template, and to employ a shifted deflection having a smallest Euclidean distance to the current template for use in updating said current template.

32. A cardiac stimulating device as claimed in claim 31 wherein said time interval is in a range between 0 and 15 ms, and wherein said step is in a range between one and two ms.

33. A cardiac stimulating device as claimed in claim 21 wherein said processor is programmed to employ a Generalized Lloyd Algorithm to determine respective centers of said classes, for determining said at least one class most representative of a QRS complex.

34. A cardiac stimulating device as claimed in claim 21 wherein said processor is programmed to identify said at least one class that is most representative of a QRS complex as the class having a highest morphology similarity to an actual QRS complex.

35. A cardiac stimulating device as claimed in claim 21 wherein said processor is programmed to employ a Generalized Lloyd Algorithm to identify respective centers of said classes, and selecting said at least one class as most representative of a QRS complex having a minimum Euclidean distance to its class center.

36. A cardiac stimulating device as claimed in claim 21 wherein said processor is programmed to select said at least one class as most representative of a QRS complex having a largest negative magnitude.

37. A cardiac stimulating device as claimed in claim 21 wherein said processor is programmed to select said at least one class as most representative of a QRS complex having a largest positive magnitude.

38. A cardiac stimulating device as claimed in claim 21 wherein said processor is programmed to select said at least one class as most representative of a QRS complex as having a repetition rate within a normal physiological range for cardiac activity.

39. A cardiac stimulating device as claimed in claim 21 wherein said filter filters said IEGM signal during recording thereof.

40. A cardiac stimulating device as claimed in claim 21 wherein said filter filters said IEGM signal after recording thereof.

* * * * *